US012539223B2

(12) United States Patent
Tessadri et al.

(10) Patent No.: US 12,539,223 B2
(45) Date of Patent: Feb. 3, 2026

(54) ADJUSTABLE ORTHOPAEDIC BRACE

(71) Applicants: ISICO S.R.L., Milan (IT); Fabrizio Tessadri, Caldonazzo (IT)

(72) Inventors: Fabrizio Tessadri, Caldonazzo (IT); Stefano Negrini, Milan (IT)

(73) Assignees: Fabrizio Tessadri (IT); ISICO S.R.L. (IT)

( * ) Notice: Subject to any disclaimer, the term of this patent is extended or adjusted under 35 U.S.C. 154(b) by 328 days.

(21) Appl. No.: 17/800,288

(22) PCT Filed: Feb. 26, 2021

(86) PCT No.: PCT/IB2021/051628
§ 371 (c)(1),
(2) Date: Aug. 17, 2022

(87) PCT Pub. No.: WO2021/171252
PCT Pub. Date: Sep. 2, 2021

(65) Prior Publication Data

US 2023/0074390 A1 Mar. 9, 2023

(30) Foreign Application Priority Data

Feb. 26, 2020 (IT) ........................ 102020000003991

(51) Int. Cl.
*A61F 5/01* (2006.01)

(52) U.S. Cl.
CPC ........ *A61F 5/01* (2013.01); *A61F 2005/0167* (2013.01)

(58) Field of Classification Search
CPC .... A61F 5/01; A61F 5/022; A61F 5/30; A61F 5/028; A61F 5/024; A61F 5/026; A61F 5/03; A61F 5/02; A61F 2005/0167
USPC .............................................................. 602/5
See application file for complete search history.

(56) References Cited

U.S. PATENT DOCUMENTS 4,559,933 A * 12/1985 Batard .................... A61F 5/022 128/DIG. 20
6,478,759 B1 11/2002 Modglin et al.
7,316,660 B1 * 1/2008 Modglin ................. A61F 5/028 602/5
2004/0147861 A1 * 7/2004 Kozersky ................ A61F 5/022 602/5

(Continued)

FOREIGN PATENT DOCUMENTS

CN 1349395 A 5/2002
CN 101296675 A 10/2008

(Continued)

OTHER PUBLICATIONS

S-Polytec, Thermoforming of plastics, Jun. 18, 2018 (Year: 2018).*

(Continued)

*Primary Examiner* — Daniel A Miller
(74) *Attorney, Agent, or Firm* — The Belles Group, P.C.

(57) ABSTRACT

An orthopaedic brace has two rigid valves, each having a back portion; a rigid back plate extending in a longitudinal direction and partially overlapping the back portions of both valves; front closing devices, configured to tighten the valves at the front in an adjustable manner; back closing devices, configured to tighten the valves at the back in an adjustable manner.

8 Claims, 3 Drawing Sheets

(56) References Cited

U.S. PATENT DOCUMENTS

| | | | | |
|---|---|---|---|---|
| 2004/0220503 | A1 | 11/2004 | Kozersky | |
| 2005/0203453 | A1 | 9/2005 | Willner et al. | |
| 2009/0131841 | A1 | 5/2009 | Epple et al. | |
| 2010/0168630 | A1 * | 7/2010 | Cropper | A61F 5/024<br>602/19 |
| 2014/0283845 | A1 | 9/2014 | Slusarz, Jr. | |
| 2017/0246338 | A1 * | 8/2017 | Taylor | A61F 13/04 |

FOREIGN PATENT DOCUMENTS

| | | | | | |
|---|---|---|---|---|---|
| CN | 105338896 | A | | 2/2016 | |
| CN | 110772368 | A | | 2/2020 | |
| EP | 2878284 | A1 | * | 6/2015 | A61F 5/022 |
| FR | 2908295 | A1 | | 5/2008 | |
| FR | 2968540 | A1 | | 6/2012 | |
| GB | 2272160 | A | * | 5/1994 | A61F 13/04 |

OTHER PUBLICATIONS

Translation of EP 2878284 A1 (Year: 2015).*

Office Action issued in counterpart Chinese Application No. 202180016632.5 on Aug. 14, 2024.

* cited by examiner

ADJUSTABLE ORTHOPAEDIC BRACE

CROSS-REFERENCE TO RELATED APPLICATIONS

This patent application is a U.S. national stage application under 35 U.S.C. § 371 of PCT application no. PCT/IB2021/051628, filed on Feb. 26, 2021, which claims priority from Italian patent application no. 102020000003991 filed on Feb. 26, 2020. The entire disclosure of the aforementioned priority applications are incorporated herein by reference in their entireties.

TECHNICAL FIELD

The present invention relates to an orthopaedic brace.

BACKGROUND ART

As is known, the treatment of some pathologies of the spinal column of moderate or severe degree, including spinal deformities and in particular scoliosis, requires the use of orthopaedic braces.

Generally, orthopaedic braces comprise two rigid valves and front closing devices for tightening at the front the orthopaedic brace once the orthopaedic brace has been put on by the patient.

Compared to plaster-of-Paris jackets, of which the mechanical properties can be achieved, orthopaedic braces are generally better tolerated, both because the risk of causing sores is lower, and because orthopaedic braces have the advantage that they can be put on and removed with greater easiness, for example for enabling the daily activities of hygiene and of change of underclothes. Tolerability for patients is a decisive factor for the effectiveness of the treatments and can constitute a limit to the diffusion, especially of some types of orthopaedic braces.

A limit of the known braces, especially of those having greater rigidity, which are more effective also for the more severe pathologies, is connected to the fact that the production can be only partially industrialized.

The currently available braces, in fact, are custom made for the patient and are nearly devoid of the possibility of adjustment between the respective parts once these have been definitively fixed.

Because of the limited possibility of adjustment, orthopaedic braces have to necessarily be custom made for each patient and in practice it is not possible to exploit industrial techniques that reduce manufacturing costs. Likewise, it is not possible to adapt the shape of the orthopaedic brace when the posture of the patient modifies as a consequence of the treatment or of growth. In practice, it can happen that, after the first step of the treatment or due to the changed physical conditions of the patient, the orthopaedic brace is no longer fit to correctly transmit the forces and, after an initial step, the treatment loses its optimal effectiveness.

Furthermore, in the currently known braces, the difficulty and the limitedness of the adjustments that can be carried out typically require the intervention of specialised technical personnel and a great amount of time, not being anyway fully effective.

A further drawback is the use of materials having a strong environmental impact for the manufacturing of the braces of known type, which are typically manufactured using a remarkable amount of plaster or disposable foam with consequent disposal problems.

DISCLOSURE OF INVENTION

The object of the present invention is to provide an adjustable orthopaedic brace which allows overcoming or at least mitigating the described limits.

Therefore, according to the present invention, an orthopaedic brace is provided comprising two rigid valves, each having a back portion; a rigid back plate extending in a longitudinal direction and partially overlapping the back portions of both valves; front closing devices, configured to tighten the valves at the front in an adjustable manner; back closing devices, configured to tighten the valves at the back in an adjustable manner.

Thanks to the present invention, it is possible to adjust the brace in an extremely rapid and effective manner without having to use machinery and technical personnel specialised in the field of reference. In particular, it is possible to adjust the brace both at the front and at the back so as to accurately adapt the valves to the anthropometric characteristics of a specific patient. The adjustable plate ensures a wide range of back adjustment simultaneously ensuring a suitable rigidity of the brace.

Furthermore, it is possible to readapt the brace in an equally simple and rapid manner subsequent to variations of the physical characteristics of the patient and rapid morphological changes of the patient caused by the continuous corrective thrust of the brace. In this manner, it is possible to maintain the effectiveness constant during the entire duration of the treatment and reduce the number of times in which it is necessary to change the brace.

Advantageously, the manufacturing process of the brace can be easily industrialized, since the great adaptability to the physical characteristics of the patient allows the production in series of the components of the brace, in particular of the valves and of the back plate. Therefore, it is no longer necessary to manufacture the orthopaedic brace from the very beginning with the exact measures of the patient with a consequent reduction in costs and an increased accessibility to the aid.

According to an aspect of the invention, the back plate follows the shape of the back portions of the valves so as to provide a suitable support to the rachis of the patient simultaneously limiting the dimensions in sagittal direction.

According to an aspect of the invention, the back plate overlaps the back portion of each of the valves for a width comprised between 2 and 5 centimetres in a direction transverse to the longitudinal direction.

According to an aspect of the invention, the valves are made of a first material and the back plate is made of a second material having stiffness greater or equal to the stiffness of the first material.

According to an aspect of the invention, the back plate is made of thermoformable material at temperatures comprised between 140° C. and 240° C., preferably between 170° C. and 210° C.

In this manner, it is possible to increase the industrialization of the back plate, which can be manufactured in nearly standardized dimensions or sizes and subsequently adapted to the physical characteristics of the specific patient.

Furthermore, it is possible to readapt the back plate to the shape of the patient in a simple and cost-effective manner subsequent to changes in the physical characteristics of the patient, due, for example, to the treatment itself.

In particular, the back plate is made of rigid polyethylene, so as to simultaneously ensure its thermoformability and a suitable stiffness.

Furthermore, the use of such material limits the environmental impact of the brace.

According to an aspect of the invention, each back closing device is coupled to the back portion of a respective one of the valves and to the back plate.

In this manner, it is possible to tighten and adjust the brace at the back in a simple and effective manner.

According to an aspect of the invention, each back closing device comprises a retaining element connected to the back portion of a respective one of the valves, and a belt connected to the back plate and to the respective retaining element; the retaining elements being configured to accommodate the respective belts in a sliding manner in an adjustment position and to lock the respective belts in a position of use; preferably the retaining element comprising a buckle or a clip or a snap fastener.

In this manner, it is possible to limit the thickness and the dimensions of each back closing device in sagittal direction, answering the need to make the brace not very visible when the patient wears the brace under the clothes.

According to an aspect of the invention, each belt is fixed by means of a fixing element to the back portion of the same valve to which the respective retaining element is connected.

In other words, each back closing device is configured to adjust the relative position between the back plate and the back portion to which it is fixed.

According to an aspect of the invention, at least one belt comprises a first portion extending between the fixing element and the back plate, and a second portion extending between the back plate and the retaining element; the first and the second portions defining an angle comprised between 15° and 45°.

In this manner, it is possible to tighten the brace and fasten the back plate in the correct position along the longitudinal direction in a simple and precise manner.

According to a further aspect of the invention, each back closing device is coupled to the back portions of both valves and to the back plate.

In particular, each back closing device comprises a retaining element connected to the back portion of one of the two valves, and a belt fixed by means of a fixing element to the back portion of the other of the two valves; the retaining elements being configured to accommodate the respective belts in a sliding manner in an adjustment position and to lock the respective belts in a position of use; preferably the retaining element comprising a buckle or a clip or a snap fastener.

In this manner, it is possible to limit the number of the back closing devices so as to make the adjustment and the closing of the brace even faster.

According to an aspect of the invention, the back closing devices comprise, for each valve, dorsal closing devices, sacral closing devises and lumbar closing devices arranged between the dorsal closing devices and the sacral closing devices in relation to the longitudinal direction.

In particular, the dorsal closing devices and the sacral closing devices are tilted at opposite angles to each other, so as to put in traction the back plate along the longitudinal direction once tightened, ensuring the correct positioning of the back plate along the longitudinal direction.

According to an aspect of the invention, each valve comprises a respective pelvic portion at least partially made of a thermoformable polymeric material having a softening point comprised between 45° C. and 80° C.

The low softening point of the thermoformable material allows making the pelvic portions mouldable at temperatures that can be safely stood by the patient. The forming of the pelvic portions can thus be carried out directly on the patient, obtaining the maximum adaptability of the same. Furthermore, it is no longer necessary to manufacture the orthopaedic brace from the very beginning with the exact measures of the patient.

On the other hand, the thermoforming process can be repeated every time it is necessary, in particular to adapt the pelvic portions as the shape of the patient modifies as a consequence of the treatment, of the pathology and/or of growth. In this manner, it is possible to maintain the maximum effectiveness during the entire duration of the treatment.

BRIEF DESCRIPTION OF THE DRAWINGS

Further characteristics and advantages of the present invention will be evident from the following description of non-limiting embodiment examples, with reference to the figures of the accompanying drawings, wherein.

BEST MODE FOR CARRYING OUT THE INVENTION

Figure 3:
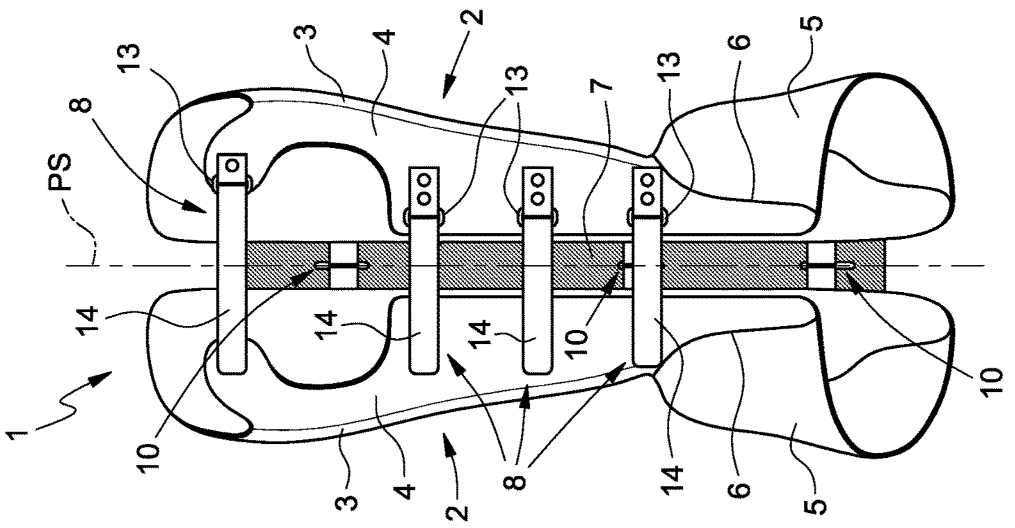
FIG. 3 is a front orthogonal view of the orthopaedic brace of FIG. 1.
Figure 2:
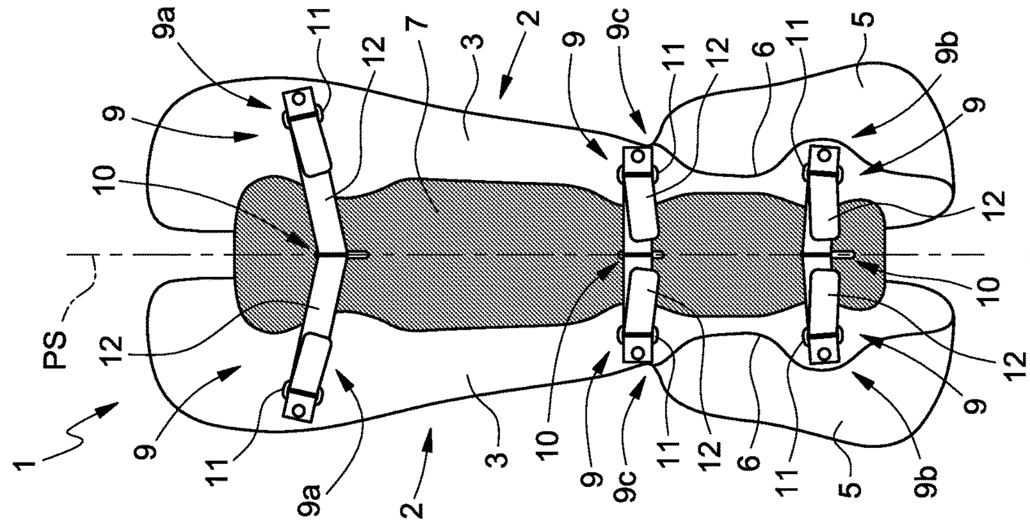
FIG. 2 is a back orthogonal view of the orthopaedic brace of FIG. 1.
Figure 1:
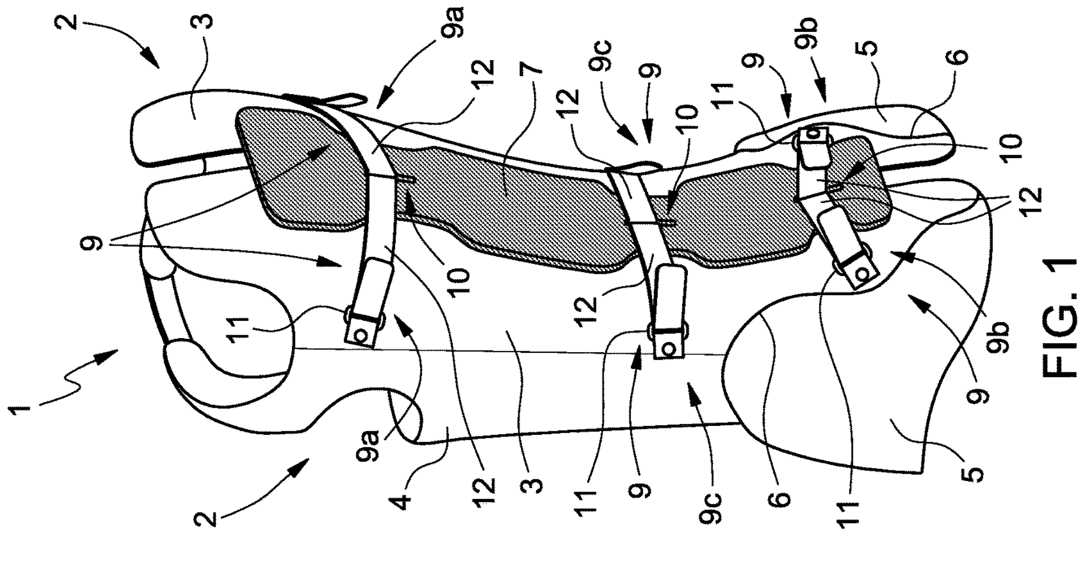
FIG. 1 is a back perspective view of an orthopaedic brace in accordance with an embodiment of the present invention.

With reference to FIGS. 1-3, an orthopaedic brace in accordance with an embodiment of the present invention is indicated with reference numeral 1 and comprises two rigid valves 2, each having a back portion 3, a front portion 4 and a pelvic portion 5.

Each valve 2 is shaped so as to wrap around a respective half of a torso of a patient at the back, on one side and at the front.

In particular, the valves 2 are arranged at a distance from each other and are opposite with respect to the median sagittal plane PS.

According to the treatment indications, the valves 2 can or cannot be symmetric.

In particular, each front portion 4 is rigidly connected to the respective back portion 3.

In accordance with an embodiment of the present invention, each valve 2 is manufactured in a single piece. In other words, the back portion 3 and the front portion 4 constitute a single piece.

In accordance with a variant of an embodiment, the back portion 3 and the front portion 4 are manufactured as separate parts and subsequently joined to each other, so as to rigidly connect the back portion 3 and the front portion 4.

Each pelvic portion 5 is a shell surrounding a respective hemipelvis of the patient when the orthopaedic brace 1 is worn, and is rigidly connected to the respective back portion 3 and to the respective front portion 4.

In particular, each pelvic portion 5 is connected to the respective back portion 3 and to the respective front portion 4 along a junction arch 6 extending around the hips. The connection can be obtained for example by means of welding, gluing, riveting or with any technique suitable for producing a rigid fixing.

In accordance with an alternative embodiment, each pelvic portion 5, the respective back portion 3 and the respective front portion 4 constitute a single piece. In other words, each valve 2 is manufactured as a single piece comprising the back portion 3, the front portion 4 and the pelvic portion 5.

The brace 1 further comprises a rigid back plate 7, which extends in a longitudinal direction and partially overlaps the back portions 3 of both valves 2; front closing devices 8, configured to tighten the valves 2 at the front in an adjustable manner; back closing devices 9, configured to tighten the valves 2 at the back in an adjustable manner.

In particular, the back plate 7 follows the shape of the back portions 3 of the valves 2 and, in use, is arranged in contact with both back portions 3.

More specifically, the back plate 7 is arranged so as to fill the back distance between the valves 2 and overlaps each back portion 3 for a width comprised between 2 and 5 centimetres in a direction transverse to the longitudinal direction.

In accordance with an embodiment, the back portion 7 is provided with seats 10 for the coupling to the back closing devices 9. In the non-limiting case of the present invention described and illustrated herein, the seats 10 are through openings made in the back plate 7.

The valves 2 are made of a first material; the back plate 7 is made of a second material having stiffness greater or equal to the stiffness of the first material.

The back plate 7 is made of any material having high resistance to the deforming forces which can be progressively modified in a simple and stable manner.

In particular, the back plate 7 is made of thermoformable material, preferably of a thermoformable polymeric material. More specifically, the forming of the back plate 7 occurs between 140° C. and 240° C., preferably between 170° C. and 210° C. In accordance with an embodiment, the back plate 7 is made of rigid polyethylene.

In accordance with an alternative embodiment, the back plate 7 is made of a ductile and deformable metal material, preferably of aluminum.

In an embodiment, the first material forming the valves 2 can be a polymeric material, preferably high-density polyethylene (HDPE). In a different embodiment, the valves 2 can be made of a composite material comprising carbon fibers embedded in a matrix.

With reference to the case of FIGS. 1 and 2, each back closing device 9 is coupled to a respective back portion 3 and to the back plate 7.

In other words, each back closing device 9 operates between one of the two back portions 3 and the back plate 7.

In particular, each back closing device 9 comprises a retaining element 11 connected to a respective back portion 3, and a belt 12 connected to the back plate 7 and to the respective retaining element 11.

More specifically, each belt 12 engages a respective seat 10.

The retaining elements 11 are configured to accommodate the respective belts 12 in a sliding manner in an adjustment position and to lock the respective belts 12 preventing the sliding in a locking position. In the non-limiting case of the present invention described and illustrated herein, the retaining element 11 comprises a buckle. In this case, the retaining element 11 is in the position of use when the buckle is substantially coplanar with the portion of belt 12 coupled thereto and in an adjustment position otherwise. In accordance with further embodiments, not shown in the accompanying figures, each back closing device 9 can comprise different types of retaining elements, such as for example clips or snap fasteners.

In accordance with alternative embodiments, not illustrated in the accompanying figures, the belt 12 can be replaced with a strap or with any other connection element adapted to couple each back portion 3 to the back plate 7, without departing from the scope of protection of the present invention. In an embodiment, in particular, the belt 12 can be replaced by a rod with asymmetrical teeth with a steep front and the retaining element 11 can comprise a beak coplanar with the teeth, which engages the steep front of the teeth allowing the sliding of the rod in one single direction.

In particular, the brace 1 comprises, for each valve 2, dorsal closing devices 9*a*, sacral closing devices 9*b* and lumbar closing devices 9*c* arranged between the dorsal closing devices 9*a* and the sacral closing devices 9*b* in relation to the longitudinal direction.

The dorsal closing devices 9*a* and the sacral closing devices 9*b* are tilted at opposite angles to each other. The lumbar closing devices 9*c* extend in a direction substantially perpendicular with respect to the median sagittal plane PS.

The number and the arrangement of the back closing devices 9 described and illustrated herein is merely exemplifying of the present invention and is not to be understood as limiting.

With reference to FIG. 3, each front closing device 8 is coupled to both front portions 4.

In other words, each front closing device 8 operates between the front portions 4 of the two valves 2.

In particular, each front closing device 8 comprises a retaining element 13 connected to one of the two front portions 4, and a belt 14 connected to the other between the two front portions 4 and to the respective retaining element 13.

In the non-limiting case of the present invention described and illustrated herein, the retaining element 13 comprises a buckle. In accordance with further embodiments, not shown in the accompanying figures, each front closing device 8 comprises different types of retaining elements, such as, for example, clips or snap fasteners.

In accordance with alternative embodiments, not illustrated in the accompanying figures, the belt 14 can be replaced with a strap or with any other connection element adapted to couple the two front portions 4, without departing from the scope of protection of the present invention.

In particular, the brace 1 comprises four front closing devices 8 extending in a direction substantially perpendicular with respect to the median sagittal plane PS.

The number and the arrangement of the front closing devices 8 described and illustrated herein, is merely exemplifying of the present invention and is not to be understood as limiting.

With reference to FIGS. 1-3, after the brace 1 has been put on by the patient, the belts 12 and 14 are pulled or released with the respective retaining elements 11 and 13 in an adjustment position so as to adjust the brace 1 with precision adapting it to the specific anthropometric characteristics of the patient. Once completed the adjustment, the belts 12 and

14 are tightened by means of the respective retaining elements 11 and 13, which are arranged in the position of use so as to lock the valves 2 in the desired position.

When, subsequent to the changes in the physical shape of the patient, due for example to the treatment itself, the brace 1 is not fully effective for the treatment of the patient, the back plate 7 can be replaced with a further back plate 7 shaped in a different manner or its shape can be varied by means of thermoforming, in order to readapt the brace 1 to the changed physical characteristics of the patient.

Figure 4:
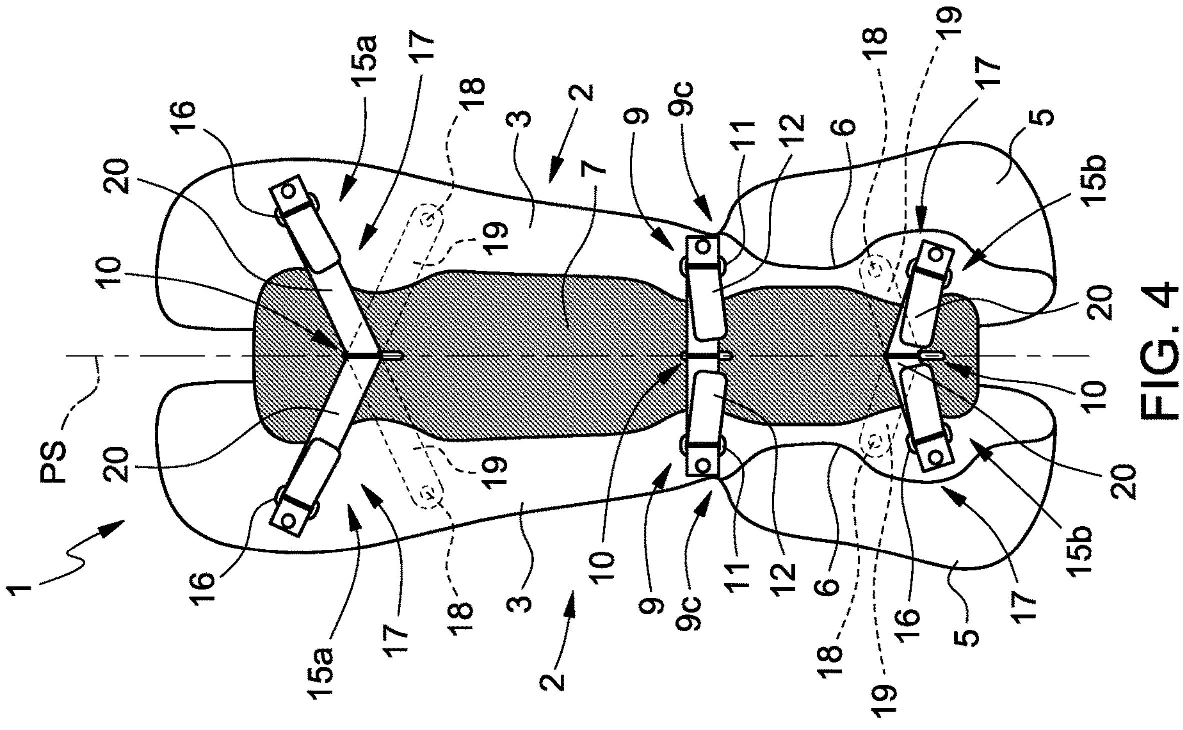
FIG. 4 is a back orthogonal view of an orthopaedic brace in accordance with a different embodiment of the present invention.

According to an embodiment of the invention, illustrated in FIG. 4, the brace 1 comprises dorsal closing devices 15*a* and sacral closing devices 15*b*, each of which is provided with a retaining element 16, connected to one of the two back portions 3, and a belt 17 fixed by means of a fixing element 18 to the same back portion 3 to which the respective retaining element is connected 16.

In other words, each belt 17 is fixed to the respective back portion 3, engages the respective seat 10 and is coupled to the respective retaining element 16, which is connected to the back portion 3 to which the belt 17 is connected.

In particular, the belt 17 is fixed by means of the fixing element 18 to an inner face of the respective back portion 3, faced, in use, towards the torso of the patient, and the retaining element 16 is connected to an outer face of the respective back portion 3, opposite to said inner face.

More specifically, each belt 17 comprises a portion 19 extending between the fixing element 18 and the back plate 7, and a portion 20 extending between the back plate 7 and the retaining element 16. The portions 19 and 20 define an angle $\alpha$ comprised between 15° and 45°.

Figure 5:
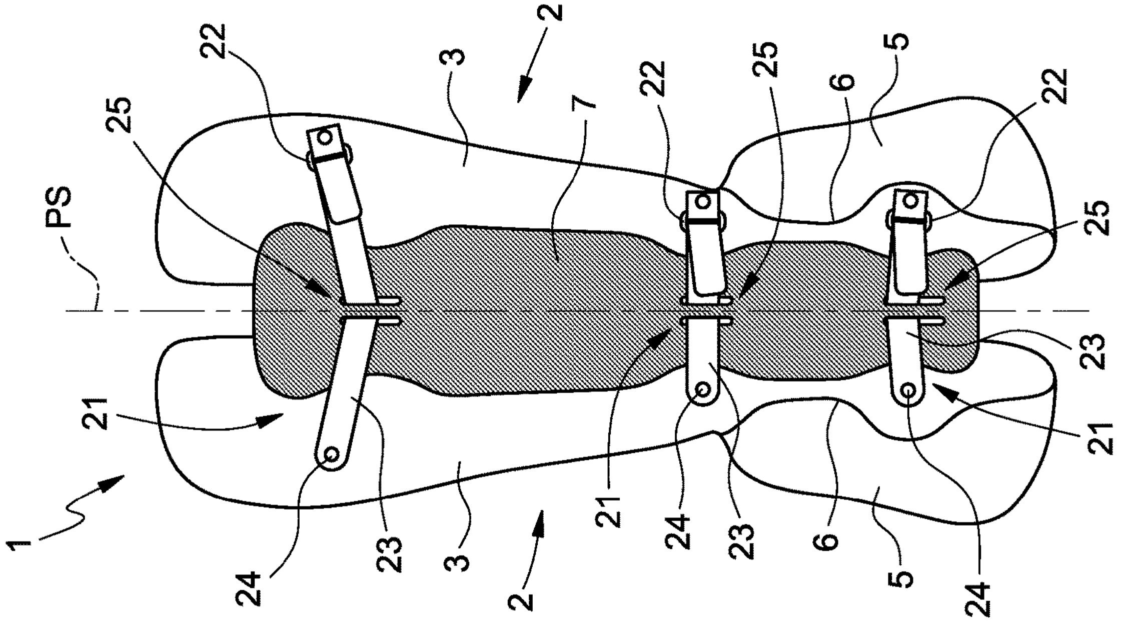
FIG. 5 is a back orthogonal view of an orthopaedic brace in accordance with another embodiment of the present invention.

According to an embodiment of the invention, illustrated in FIG. 5, the brace 1 comprises three back closing devices 21, each of which is coupled to the back portions 3 of both valves 2 and to the back plate 7.

In particular, each back closing device 21 comprises a retaining element 22 connected to one of the two back portions 3, and a belt 23 fixed by means of a fixing element 24 to the other of the two back portions 3 and to the respective retaining element 22.

More specifically, the back plate 7 comprises seats 25 for the coupling to a respective back closing device 21. In the non-limiting case of the present invention described and illustrated herein, each seat 25 comprises a pair of openings made in the back plate 7. In use, the belt 23 engages the openings of the respective seat 25.

Figure 6:
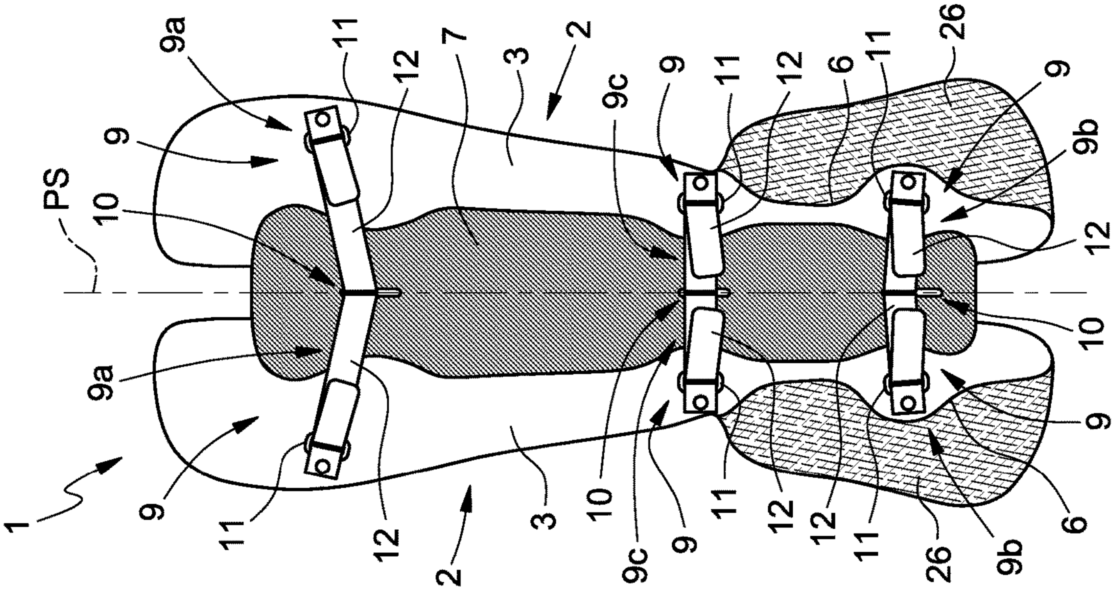
FIG. 6 is a back orthogonal view of an orthopaedic brace in accordance with a further embodiment of the present invention.

According to an embodiment of the invention, illustrated in FIG. 6, each valve 2 comprises a respective pelvic portion, indicated herein with reference numeral 26. Each pelvic portion 26 is at least in part made of a thermoformable polymeric material having a softening point comprised between 45° C. and 80° C.

Figure 7:
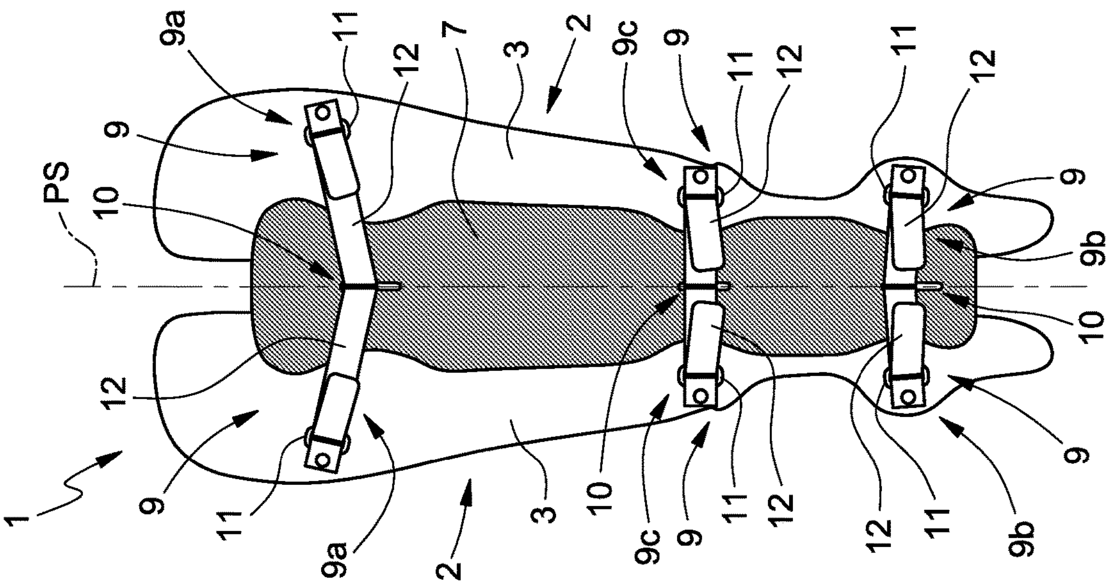
FIG. 7 is a back orthogonal view of an orthopaedic brace in accordance with a further embodiment of the present invention.

According to an embodiment of the invention, illustrated in FIG. 7, each valve 2 is devoid of a pelvic portion of the type indicated with reference numeral 5 in FIGS. 1-6.

Finally, it is to be understood that modifications and variants can be made to the described and claimed orthopaedic brace without thereby departing from the scope of protection defined by the appended claims.

The invention claimed is:

1. An orthopedic brace comprising two rigid valves, each having a back portion; a rigid back plate extending in a longitudinal direction and partially overlapping the back portions of both rigid valves; front closing devices, configured to tighten the rigid valves at a front in an adjustable manner; back closing devices, configured to tighten the rigid valves at a back in an adjustable manner;

wherein each back closing device is coupled to the back portion of a respective one of the rigid valves and to the rigid back plate;

wherein each back closing device comprises a retaining element connected to the back portion of a respective one of the rigid valves, and a belt connected to the rigid back plate and to the respective retaining element; the retaining elements being configured to accommodate the respective belts in a sliding manner in an adjustment position and to lock the respective belts in a position of use, wherein each belt is fixed by a fixing element to the back portion of the same rigid valve to which the respective retaining element is connected, and wherein at least one belt of the back closing devices comprises a first portion extending between the fixing element and the rigid back plate, and a second portion extending between the rigid back plate and the retaining element; the first and the second portions defining an angle comprised between 15° and 45°.

2. The orthopedic brace according to claim 1, wherein the back closing devices comprise, for each rigid valve, dorsal closing devices, sacral closing devices, and lumbar closing devices, wherein the lumbar closing devices are arranged between the dorsal closing devices and the sacral closing devices in relation to the longitudinal direction.

3. The orthopedic brace according to claim 2, wherein the dorsal and sacral closing devices are tilted at opposite angles to each other.

4. The orthopedic brace according to claim 1, wherein the rigid back plate follows a shape of the back portions of the rigid valves.

5. The orthopedic brace according to claim 1, wherein the rigid back plate overlaps the back portion of each of the rigid valves for a width between 2 and 5 centimeters in a direction transverse to the longitudinal direction.

6. The orthopedic brace according to claim 1, wherein the rigid valves are made of a first material and the rigid back plate is made of a second material having a stiffness greater or equal to the stiffness of the first material.

7. The orthopedic brace according to claim 1, wherein the rigid back plate is made of thermoformable material, which, in particular, is thermoformable at temperatures between 140° C. and 240° C. or between 170° C. and 210° C.

8. The orthopedic brace according to claim 1, wherein the rigid back plate is made of rigid polyethylene.

* * * * *